US005958415A

United States Patent [19]
Yuuki et al.

[11] Patent Number: 5,958,415
[45] Date of Patent: *Sep. 28, 1999

[54] PROTEIN ALLERGEN OF DERF II AND COMPOSITION

[75] Inventors: Toshifumi Yuuki; Yasushi Okumura, both of Tokyo; Hiroshi Yamakawa, Urayasu, all of Japan

[73] Assignees: Asahi Breweries, Ltd.; Torii & Co., Ltd., both of Tokyo, Japan

[*] Notice: This patent is subject to a terminal disclaimer.

[21] Appl. No.: 08/905,801

[22] Filed: Aug. 12, 1997

Related U.S. Application Data

[62] Division of application No. 08/288,888, Aug. 10, 1994, Pat. No. 5,798,099, which is a continuation of application No. 07/658,596, Feb. 21, 1991, abandoned.

[30] Foreign Application Priority Data

Mar. 3, 1990 [JP] Japan ........................................ 2-50848

[51] Int. Cl.⁶ .................... A61K 39/00; A61K 39/385; A61K 39/35; C07K 1/00
[52] U.S. Cl. .................................... 424/185.1; 424/193.1; 424/275.1; 530/350; 530/395
[58] Field of Search ..................................... 530/350, 395; 424/185.1, 193.1, 275.1

[56] References Cited

U.S. PATENT DOCUMENTS

| | | |
|---|---|---|
| 4,837,148 | 6/1989 | Cregg . |
| 4,879,213 | 11/1989 | Fox et al. . |
| 5,433,948 | 7/1995 | Thomas et al. . |
| 5,552,142 | 9/1996 | Thomas et al. . |
| 5,798,099 | 8/1998 | Yuuki et al. . |

FOREIGN PATENT DOCUMENTS

WO 88/10297  12/1988  WIPO .

OTHER PUBLICATIONS

Bowie et al, "Deciphering the message in protein sequences: Tolerance to amino acid substitutions", *Science* 247:1306–1310 (1990).

Chua et al, "Sequence analysis of cDNA coding for a major house dust mite allergen, *Der p* I", *J. Exp. Med.* 167:175–182 (Jan. 1988).

Chua et al, "Isolation of cDNA coding for the major mite allergen *Der p* II by IgE plaque immuno–assay", *Int. Arch. Allergy Appl. Immunol.* 91:118–123 (1990).

Chua et al, "Expression of *Dermatophagoides pteronyssinus* allergen, *Der p* II, in *Escherichia coli* and the binding studies with human IgE", *Int. Arch. Allergy Appl. Immunol.* 91:124–129 (1990).

Ford et al, "Standardization of *Dermatophagoides pteronyssinus*: Assessment of potency and allergen content in ten coded extracts", *Int. Archs Allergy Appl. Immun.* 76:58–67 (1985).

Greene et al, "Antigenic analysis of group I house dust mite allergens using random fragments of *Der p* I expressed by recombinant DNA libraries", *Int Arch Allergy Appl Immunol* 92:30–38 (1990).

Haida et al, "Allergens of the house dust mite *Dermatophagoides farinae*—Immunochemical studies of four allerlgenic fractions", *J. Allergy Clin. Immunol.* 75(6):686–692 (Jun. 1985).

Heymann et al, "Antigen *Der f* I from the dust mite *Dermatophagoides farinae*: Structural comparison with *Der p* I from *Dermatophagoides pteronyssinus* and epitope specificity of murine IgG and human IgE antibodies", *The Journal of Immunology* 137:2841–2847 (1986).

Ino et al, "Characterization of the proteases in the crude mite extract", *Int Arch Allergy Appl Immunol* 89:321–326 (1989).

Kumar et al, "Amino acid variations at a single residue in an autoimmune peptide profoundly affect its properties: T–cell activation, major histocompatibility complex binding, and ability to block experimental allergic encaphalomyelitis", *Proc. Natl. Acad. Sci. USA* 87:1337–1341 (1990).

Maniatis et al, *Molecular Cloning: A Laboratory Manual*. Cold Spring Harbor, 1982, pp. 226–228, 411–413 and 422 (1982).

Stewart et al, "In vitro translation of messenger RNA from the house dust mite *Dermatophagoides pteronyssinus*", *Int. Archs Allergy Appl. Immun.* 83:384–389 (1987).

Suggs et al, "Use of synthetic oligonucleotides as hybridization probes: Isolation of cloned cDNA sequences for human beta2–microglobulin", *Proc. Natl. Acad. Sci. USA* 78(11):6613–6617 (1981).

Thomas et al, "Cloning and expression of DNA coding for the major house dust mite allergen *Der p* 1 in *Escherichia coli*", *Int. Archs Allergy Appl. Immun.* 85:127–129 (1988).

Thomas et al, "Analysis and expression of cDNA clones coding for house dust mite allergens", *Advances in Biosciences* 74:139–147 (1989).

Tovey et al, "Cloning and sequencing of a cDNA expressing a recombinant house dust mite protein that binds human IgE and corresponds to an important low molecular weight allergen", *J. Exp. Med.* 170:1457–1462 (1989).

Yamashita et al, "Allergens of the house dust mite *Dermatophagoides farinae*. II. Immunological characterization of four allergenic molecules", *Int Arch Allergy Appl Immunol* 88:173–375 (1988).

Yasueda et al, "Isolation and characterization of two allergens from *Dermatophagoides farinae*", *Int. Archs Allergy Appl. Immun.* 81:214–223 (1986).

Yasueda et al, "Comparative analysis of physicochemical and immunochemical properties of the two major allergens from *Dermatophagoides pteronyssinus* and the corresponding allergens from *Dermatophagoides farinae*", *Int Arch Allergy Appl Immunol* 88:402–407 (1989).

(List continued on next page.)

Primary Examiner—Anthony C. Caputa
Assistant Examiner—Mark Navarro
Attorney, Agent, or Firm—Browdy and Neimark

[57] ABSTRACT

The invention provides at least one protein which has biochemical and immunological properties of a major allergen of *Dermatophagoides farinae* (Derf II).

5 Claims, No Drawings

OTHER PUBLICATIONS

Yasueda et al, "Measurement of allergens associated with dust mite allergy", *Int Arch Allergy Appl Immunol* 90:182–189 (1989).

Young et al, "Efficient isolation of genes by using antibody probes", *Proc. Natl. Acad. Sci. USA* 80:1194–1198 (1983).

Yuuki et al, "Cloning and sequencing of cDNAS corresponding to mite major allergen *Der f* II", *Jpn. J. Allergol.* 39:557–561 (1990).

Chapman et al, Epitope mapping of major dust mite (dermatophagoides) allergens using monoclonal antibodies. In: *Mite Allergy* (Eds. A.L. de Weck, A. Todt), The UCB Institute of Allergy, Brussels, pp. 27–29, 1987.

PROTEIN ALLERGEN OF DERF II AND COMPOSITION

CROSS REFERENCE TO RELATED APPLICATIONS

The present application is a division of application Ser. No. 08/288,888, filed Aug. 10, 1994, now U.S. Pat. No. 5,798,099, which is a continuation of application Ser. No. 07/658,596, filed Feb. 21, 1991, now abandoned.

BACKGROUND OF THE INVENTION

The present invention relates to DNAs encoding a major allergen of house dust mites, replication vectors, plasmids and host cells which have a concern in the DNAs, and the use thereof.

Allergic diseases generally have several kinds of symptoms which are developed by sensitization of antigen causing the diseases, in which IgE antibody (reagin antibody) specific for allergen in blood serum and tissue is produced, the antibody is exposed again to the antigen and the antibody reacts with the antigen in each tissue.

There is a desensitization therapy as a method for curing drastically the allergic diseases. In the method, the causative antigen is repeatedly administered to a patient in small doses, while the dose is gradually increased according to the symptoms. It is considered that, by the therapy, blocking antibody is produced, the production of the IgE antibody is controlled and the amount of histamine derived from a mast cell is lowered to give treatment effect.

On the other hand, it appears that allergic diseases such as bronchial asthma, childhood asthma, atopic dermatitis and the like are mainly caused by allergy to mites living in house dust. Several kinds of proteins of major mite allergens have been identified (Platts-Mills et al., J. Allergy Clin. Immunol., 80, 755 (1987)). The above desensitization therapy of the allergic diseases which uses the major allergens is very effective. However, it is impossible to prepare a large amount of purified allergens which are required in the therapy.

SUMMARY OF THE INVENTION

The inventors of the present invention have found that the above problems are solved by preparing mRNA from *Dermatophagoides farinae* and making a cDNA gene library corresponding to the mRNA, and by isolating a clone expressing Derf II, one of the major allergens, by a colony-immunoassay and isolating DNA fragments containing the objective gene from the clone.

Accordingly, objects of the present invention is to provide a DNA sequence coding the major allergen of mites in genetic engineering and to provide a method for producing a large amount of the objective allergen by expressing and preparing the major mite allergen encoded by the DNA.

The present invention provides a DNA encoding at least one part of genetic information of protein which has biochemical and immunological properties of a major allergen of *Dermatophagoides farinae* (Derf II).

DETAILED DESCRIPTION OF THE INVENTION

To obtain a gene which codes the major mite allergen Derf II, mites are artificially bred with feed or a feed composition for breeding animals such as experimental animals, domestic animals, pet animals and the like, and then the mite bodies can be isolated by a method, for example, a method disclosed in Japanese Patent Unexamined Publication No. 49-69820/1974. To obtain mRNA from the mite bodies, for example, a method disclosed by Chirgwin J. M. et al. is usable (Biochemistry 18, 5294–5299 (1979)). Moreover, a commercially available RNA extraction kit (manufactured by Amersham Company, trade name: RPN. 1264) is usable. In general eukaryotic mRNAs having a poly (A) tail at the 3' terminal can be easily purified by an affinity chromatography over oligo (dT) cellulose (Auffray C. et al., Eur. J. Biochem., 107, 303–304 (1980) ). Further, a commercially available mRNA purification kit (manufactured by Pharmashia Company, trade name: mRNA purification kit 27-9258-01) can be used conveniently.

The mRNA purified is used as a template for synthesizing the first strand of cDNA with reverse transcriptase and primer. Oligo (dT) or synthesized primer may be used. The second strand of cDNA can be synthesized by conventional methods (Huynh, T. V. et al., DNA cloning, Vol. 1, chapter 2, pp 49–78 (1985), edited by D. M. Glover). A commercially available kit for making cDNA (manufactured by Amersham Company, trade name: RPN. 1256Y) may be also used. The resulting double-stranded cDNA is inserted into a cloning site of a suitable vector, preferably, plasmid pUEX1 (Bressan G. and Stanley K., Nucl. Acids Res., 15, 10056 (1987)). Conventional methods are usable for the insertion of the double-stranded cDNA (Maniatis T. M. et al., Molecular Cloning, Cold Spring Harbor Laboratory, (1982)). The cDNA gene library derived from the mites can express a gene product by transformation of a suitable host, preferably *Escherichia coli*.

Then, a colony which is producing the desired major mite allergen Derf II should be found from the transformed *Escherichia coli*. Although several other methods are usable, colony immunoassay is suitable for that purpose. For example, the following method can be used with pUEX1 as the plasmid.

After the *E. coli* transformed was grown in an L broth agar culture (1% bactotrypton, 0.5% yeast extract, 0.5% sodium chloride, 1.5% bactoagar, 50 μg/ml ampicillin, pH 7.4), the resulting colonies were replicated on a nitrocellulose filter to grow them and recombinant protein was allowed to express on the filter. The cells were lysed by exposure to chloroform vapor and the protein expressed was fixed on the filter.

The inserted DNA derived from the mites bound to the down stream of the DNA encoding β-galactosidase, and the corresponding protein was produced in the form of protein fused together with β-galactosidase. The desired Derf II protein was detected on the filter by using an anti Derf II antibody which was prepared from a rabbit, and two positive clones were obtained. The corresponding *E. coli* colonies were selected from the master agar plate preserved, and they were inoculated to an L broth culture (removing agar from the L broth agar culture). The colonies were cultured with shaking at 30° C. for about 18 hours. The cells were collected from the culture, and plasmids were recovered by a conventional alkali extraction method. The plasmids obtained were digested or not digested. An agarose gel electrophoresis procedure is followed for analyzing DNAs derived from mites which were inserted into the plasmids. About 500 base pairs of DNAs were inserted into the two plasmids pFL1 and pFL11, respectively.

On the other hand, *E. coli* cells were transformed by using the plasmids and vector pUEX1 into which the DNA derived from mites was not inserted, and they were inoculated into the above L broth culture. The cells were cultured with shaking at 30° C. for about three hours and then at 42° C. for about three hours. The resulting cells were collected and washed in a buffer solution (Tris-HCl buffer, 10 mM, pH 7) and fusion protein was extracted by a method of Marston and Carroll et al. (DNA cloning, IRL Press, Volume 3, Chapter 4 (1985)). The proteins extracted were subjected to SDS-polyacrylamide gel electrophoresis. Then, the protein separated on the gel was transferred onto a cellulose filter by a Western blot technique (Towbin H. et al., Proc. Natl. Acad. Sci., U.S.A., 76, 4350 (1979)). The filter on which the proteins were transferred was blocked with bovine serum albumin, and it was reacted with anti-Derf II antibody which was prepared in a rabbit. Then, the filter was washed with a buffer solution (Tris-HCl buffer: 10 mM, pH 7.4, sodium chloride: 150 mM, Tween 20:0.05%), and it was reacted with anti-rabbit IgG antibody which was labelled with peroxidase (manufactured by Amersham Company). Again, the filter was washed in the same buffer solution and the peroxidase-labelled antibodies remaining without reaction was removed. Further, the filter was reacted with hydrogen peroxide and a dye of 4-chloro-1-naphthol.

As a result, while the band of protein having a molecular weight of about 130 thousand contained in the supernatant which was obtained from the *E. coli* transformed with plasmids pFL1 and pFl11 show positive, no band of protein contained in the supernatant which was obtained from the *E. coli* transformed with the vector without the DNA of ticks show positive. Accordingly, it is apparent that DNA coding Derf II which is a major mite allergen is in the plasmids pFL1 and pFL11, and the gene expresses in *E. coli* as the fused protein together with β-galactosidase.

The DNA segment derived from the mites which is inserted into said plasmids pFL1 and pFL11 can be cleaved with a suitable restriction enzyme, preferably by a complete cleavage with BamHI or partial cleavage with NcoI. The sequences of the cleaved DNA segment can be determined by a dideoxy chain termination method (Sanger F. et al., J. Mol. Biol., 162, 729–773 (1982)) and the like. The determined DNA sequences encoding the major mite allergen are shown by Formula I and Formula II. In these Formula I and Formula II, amino acids corresponding to the sequences are shown.

(SEQ ID NO:1)
Formula I:
```
  1 GGT ACC ATG GTT TCA TTG TTG GTA GCA GCC    30
  1 Gly Thr Met Val Ser Leu Leu Val Ala Ala    10

31 GTT GTT GCC GAT CAA GTC GAT GTT AAA GAT    60
 11 Val Val Ala Asp Gln Val Asp Val Lys Asp    20

61 TGT GCC AAC AAT GAA ATC AAA AAA GTA ATG    90
 21 (Cys)Ala Asn Asn Glu Ile Lys Lys Val Met    30

91 GTC GAT GGT TGC CAT GGT TCT GAT CCA TGC   120
 31 Val Asp Gly(Cys)His Gly Ser Asp Pro(Cys)   40

121 ATC ATC CAT CGT GGT AAA CCA TTC ACT TTG   150
 41 Ile Ile His Arg Gly Lys Pro Phe Thr Leu    50

151 GAA GCC TTA TTC GAT GCC AAC CAA AAC ACT   180
 51 Glu Ala Leu Phe Asp Ala Asn Gln Asn Thr    60

181 AAA ACC GCT AAA ATT GAA ATC AAA GCC AGC   210
 61 Lys Thr Ala Lys Ile Glu Ile Lys Ala Ser    70

211 CTC GAT GGT CTT GAA ATT GAT GTT CCC GGT   240
 71 Leu Asp Gly Leu Glu Ile Asp Val Pro Gly    80

241 ATC GAT ACC AAT GCT TGC CAT TTT GTC AAA   270
 81 Ile Asp Thr Asn Ala Cys His Phe Val Lys    90

271 TGT CCA TTG GTT AAA GGT CAA CAA TAT GAT   300
 91 Cys Pro Leu Val Lys Gly Gln Gln Tyr Asp   100

301 ATC AAA TAT ACA TGG AAT GTG CCG AAA ATT   330
101 Ile Lys Tyr Thr Trp Asn Val Pro Lys Ile   110

331 GCA CCA AAA TCT GAA AAC GTT GTC GTT ACA   360
111 Ala Pro Lys Ser Glu Asn Val Val Val Thr   120

361 GTC AAA CTT ATC GGT GAT AAT GGT GTT TTG   390
121 Val Lys Leu Ile Gly Asp Asn Gly Val Leu   130

391 GCT TGC GCT ATT GCT ACC CAT GGT AAA ATC   420
131 Ala Cys Ala Ile Ala Thr His Gly Lys Ile   140

421 CGT GAT TAA AAA AAA ATA AAT AAG AAA ATT   450
141 Arg Asp ***

451 TTC ACC AAC ATC GAA CAA AAT TCA ATA ACC   480

481 AAA ATT TGA ATC AAA AAA AAA AAA AAA       510

511 ACC ATG G
```

(SEQ ID NO:3)
Formula II
```
  1 GGT ACC ATG GTT TCA TTG TTG GTA GCA GCC    30
  1 Gly Thr Met Val Ser Leu Leu Val Ala Ala    10

31 GTT GTT GCC GAT CAA GTC GAT GTT AAA GAT    60
 11 Val Val Ala Asp Gln Val Asp Val Lys Asp    20

61 TGT GCC AAC AAT GAA ATC AAA AAA GTA ATG    90
 21 (Cys)Ala Asn Asn Glu Ile Lys Lys Val Met    30

91 GTC GAT GGT TGC CAT GGT TCT GAT CCA TGC   120
 31 Val Asp Gly(Cys)His Gly Ser Asp Pro(Cys)   40

121 ATC ATC CAT CGT GGT AAA CCA TTC ACT TTG   150
 41 Ile Ile His Arg Gly Lys Pro Phe Thr Leu    50

151 GAA GCC TTA TTC GAT GCC AAC CAA AAC ACT   180
 51 Glu Ala Leu Phe Asp Ala Asn Gln Asn Thr    60

181 AAA ACC GCT AAA ATT GAA ATC AAA GCC AGC   210
 61 Lys Thr Ala Lys Ile Glu Ile Lys Ala Ser    70

211 CTC GAT GGT CTT GAA ATT GAT GTT CCC GGT   240
 71 Leu Asp Gly Leu Glu Ile Asp Val Pro Gly    80

241 ATC GAT ACC AAT GCT TGC CAT TTT ATG AAA   270
 81 Ile Asp Thr Asn Ala Cys His Phe Met Lys    90

271 TGT CCA TTG GTT AAA GGT CAA CAA TAT GAT   300
 91 Cys Pro Leu Val Lys Gly Gln Gln Tyr Asp   100
```

-continued

```
301 GCC AAA TAT ACA TGG AAT GTG CCG AAA ATT    330
101 Ala Lys Tyr Thr Trp Asn Val Pro Lys Ile    110

331 GCA CCA AAA TCT GAA AAC GTT GTC GTT ACA    360
111 Ala Pro Lys Ser Glu Asn Val Val Val Thr    120

361 GTC AAA CTT GTT GGT GAT AAT GGT GTT TTG    390
121 Val Lys Leu Val Gly Asp Asn Gly Val Leu    130

391 GCT TGC GCT ATT GCT ACC CAC GCT AAA ATC    420
131 Ala Cys Ala Ile Ala Thr His Ala Lys Ile    140

421 CGT GAT TAA AAA AAA ATA AAT ATG AAA        450
141 Arg Asp ***

451 ATT TTC ACC AAC ATC GAA CAA AAT TCA ATA    480

481 ACC AAA ATT TGA ATC AAA AAA AAA AAA CCA    510

511 TGC
```

Further, the underlined parts in these formulas show the same sequences as those of amino acids shown in the following Table I. *** shows a termination codon.

To confirm the sequences of Formula I and Formula II coding Derf II which is originally the major mite allergen, the Derf II protein was purified, the amino acid sequences were determined, and the sequences were compared with the amino acid sequences shown in Formula I and Formula II. The allergen protein Derf II can be purified by a combination of conventional methods (Biochemical experimental lecture, Vol. 1, "Chemistry of protein", edited by Tamio YAMAKAWA and Kazutomo IMABORI, Tokyo Kagaku Dojin), advantageously by a liquid chromatographic technique. The amino acid sequence of the allergen Derf II purified was determined with a peptide sequencer of Type 471A (manufactured by Applied Biosystem Company). The results are shown in Table I. From these results, it was confirmed that the DNA sequences determined by the above method coded Derf II which was the major mite allergen.

TABLE I

| Analysis No. | Amino acid |
|---|---|
| 1 | Asp |
| 2 | Gln |
| 3 | Val |
| 4 | Asp |
| 5 | Val |
| 6 | Lys |
| 7 | Asp |
| 8 | X |
| 9 | Ala |
| 10 | Asn |
| 11 | Asn |
| 12 | Glu |
| 13 | Ile |
| 14 | Lys |
| 15 | Lys |
| 16 | Val |
| 17 | Met |
| 18 | Val |
| 19 | Asp |
| 20 | Gly |
| 21 | X |
| 22 | His |
| 23 | Gly |

TABLE I-continued

| Analysis No. | Amino acid |
|---|---|
| 24 | Ser |
| 25 | Asp |
| 26 | Pro |
| 27 | X |
| 28 | Ile |
| 29 | Ile |
| 30 | His |
| 31 | Arg |
| 32 | Gly |
| 33 | Lys |
| 34 | Pro |
| 35 | Phe |
| 36 | Thr |
| 37 | Leu |
| 38 | Glu |
| 39 | Ala |
| 40 | Leu |
| 41 | Phe |
| 42 | Asp |
| 43 | Ala |
| 44 | Asn |
| 45 | Gln |

The DNA segment and a part of the segment can be expressed in yeast with a suitable vector, for example, YEp13 (Broach J. R. et al., Gene, Vol. 8, 121–133 (1979)), etc. Suitable yeast cells can be transformed with a yeast vector having an expression casette carrying the mite Derf II gene according to the present invention. For the purpose, the DNA sequences according to the present invention should be placed under controlled conditions of not a *E. coli* promotor but a strong eukaryotic promotor and the like, for example delta P8 (Otake et al., Agric. Biol. Chem., Vol. 52, 2753–2762 (1988)).

The mite Derf II protein prepared by the genetic engineering technique according to the present invention, the fragments of the protein, and the protein fused with the other protein and having biochemical and immunological properties of the major mite allergen Derf II can be used in medical treatment or diagnosis of all sorts of allergic diseases caused by mites.

According to the present invention, a clone which expresses major allergen protein Derf II of *Dermatophagoides farinae* can be isolated by genetic engineering, and DNA fragments containing the desired gene can be isolated from the clone.

As a result, a mass production method of allergen protein can be provided by expressing and by obtaining the major mite allergen which is coded by DNA, and the protein can be used in medical treatment or diagnosis of all sorts of allergic diseases.

Furthermore, DNA hybridizable with and corresponding to the DNA of Formulae I and II and which codes for proteins having the biochemical and immunological properties of Derf II, can be obtained by synthesis, semisynthesis or from nature.

DESCRIPTION OF PREFERRED EMBODIMENTS

The following examples illustrate the present invention in details.

EXAMPLE 1

Construction of a cDNA Gene Library

Mites were artificially bred for about 30 days in feed for breeding experimental animals under conditions of a temperature of 25° C. and a humidity of 75%. The mites were separated from the feed with a saturated sodium chloride solution, and mites were filtered with suction (Japanese Patent Unexamined Publication No. 49-69820/1974). The mite bodies (wet weight, about 5 g) obtained were rapidly frozen in liquid nitrogen, and then total RNA was extracted and purified with an RNA extraction kit (manufactured by Amersham Company, RPN. 1264). After purifying mRNA from the total RNA with an oligo (dT) column (manufactured by Pharmacia Company, trade name: mRNA purification kit 27-9258-01), about 3 μg of mRNA was obtained. The cDNA was synthesized from the total amount of the mRNA obtained with a cDNA synthesis system plus (manufactured by Amersham Company, trade name: RPN. 1256Y). The RNA extraction, the mRNA purification and the cDNA synthesis followed manuals annexed to the kits.

pUEX1 reported by Bressan et al. (Nucl. Acids Res., Vol. 15, 10056 (1987)) was used as an expression vector. By the insertion of a cDNA fragment into the down stream of a β-galactosidase gene, the expression vector could express the desired gene as a fused protein with β-gal. The expression amount was determined by a $\lambda P_R$ promoter in the upper stream and it was greatly increased by shifting the cultivation temperature to 42° C. The cloning steps follow a method of Haymerle et al. (Nucl. Acids Res., Vol. 14, 8615–8624 (1986)) and cDNA cloning system pUEX1 (manufactured by Amersham Company, trade name: RPN. 1282) was used. E. coli MC1061 (gene type: araD139, Δ[ara, leu]7697, ΔlacX74, galU$^-$, galK$^-$, hsr$^-$, hsm$^+$, strA, mcrA$^-$, mcrB$^-$) was used for the transformation. The preparation of competent cells follows a method of Hanahan (DNA cloning, A practical approach, edited by Glover D., IRL Press, Vol. 1, 109 (1985)).

EXAMPLE 2

Detection of pFL1 and pFL11

The clones reacting with anti Derf II antibody derived from a rabbit were detected by a colony immunoassay method from the transformants. The transformants were spread on an L broth agar culture plate (1% tryptone manufactured by Difco Company, 0.5% yeast extract manufactured by Difco Company, 0.5% sodium chloride and 1.5% agar) containing 50 μg/ml of ampicillin and these strains were cultured at 30° C. to obtain colonies having a diameter of 1 mm. Nitrocellulose filters (High bond C, manufactured by Amasham Company, trade name: RPN. 1782C) were carefully placed on the colonies to make a replica of the colonies. The remaining colonies on the plate were cultured again at 30° C.

On the other hand, the replica of the colonies blotted onto the nitrocellulose filters was placed on the surface of a new L broth agar plate as the colonies were upside and the colonies were cultured at 42° C. for two hours. Then the nitrocellulose filters were hung in a tank filled with chloroform and exposed to chloroform vapor for about 25 minutes. Each filter having the colonies at the underside was placed on a petri dish. The dish was immersed into 10 ml of TBS buffer (10 mM Tris hydrochloride buffer (pH 7.4) and 150 mM sodium chloride) containing 4 mg of lysozyme and 100 μg of deoxyribonuclease and it was shaken slowly to lyse the colonies for one hour at room temperature. Washing operation was repeated four times by shaking the dish for five minutes with 20 ml of TBS buffer. Then, the filters were immersed into TBS buffer containing 2% bovine serum albumin for one hour as a blocking operation in order to prevent the nonspecific adsorption.

The filters were immersed and shaken for one hour in a solution containing the anti Derf II antibody derived from the rabbit as a primary antibody which was diluted 1000–3000 times with 10 ml of TBS buffer containing 0.2% bovine serum albumin. Then the primary antibody which was not adsorbed was washed away four times with 20 ml of TBST buffer (0.05%, TBS buffer containing Tween 20).

The same procedure as the primary antibody was repeated with filters having a peroxidase-labelled anti rabbit IgG antibody (manufactured by Biorad Company) as a secondary antibody. After adsorbing and washing the antibody, the filters were immersed in TBS buffer in which 0.4 mg/ml of diaminobenzidine as a color-producing reagent was dissolved and hydrogen peroxide water was added in end concentration of 0.01% to obtain colored filters.

The above operation was repeated with about 1600 transformed strains. Two strains of colonies giving a strong signal were found. The corresponding colonies were picked from the master plate and cultured at 30° C. to provide plasmids to be analyzed. The techniques of plasmid extraction, breakage of restriction enzyme, gel electrophoresis and the like were based on a method of Maniatis et al. (Molecular cloning, Cold Spring Harbor Press (1982)). Two kinds of E. coli thus obtained had plasmids into which segments (about 500 base pairs) derived from cDNA were inserted. These were designated as pFL1 and pFL11. These strains were deposited at the National Institute of Bioscience and Human-Technology, Agency of Industrial Science and Technology, 1–3, Higashi 1-chome, Tsukuba-shi, Ibaraki-ken 305, JAPAN, on Dec. 26, 1995, as deposit numbers FERM BP-5356 and FERM BP-5357, respectively.

EXAMPLE 3

Determination of DNA Sequence for Derf II Gene (pFL1 and pFL11)

The techniques of restriction enzyme treatment of cDNA fragments of pFL1 and pFL11 and ligation thereof and transformation of E. coli host JM105 (gene type: thi, rpsL, endA, sbcB15, hsdR4, Δ(lac-proAB), [F', proAB, lacI$^q$ΔDM15, traD36]) were carried out by conventional methods (Maniatis et al., Molecular Cloning, Cold Spring Harbor Press, p. 104, 146 and 396 (1982); DNA Cloning, IRL Press, Vol. 1, Chapter 6 (1985)). Vectors (pUC118 and pUC119, Messing et al., Methods in Enzymology, Vol. 101, 20–78 (1978)) suitable for Sanger's sequence determination (Science, Vol. 214, 1205–1210 (1985) was used for the cloning.

Thus isolated Bam HI-cDNA fragments as it was or digested with several restriction enzymes such as Nco I were inserted into vectors which were treated by the same method as described above. The E. coli competent cells were transformed. Each single-stranded DNA of the recombinant plasmids was isolated and purified, and the DNA sequence was determined by the Sanger method. The sequence was analysed by a computer program (DNASIS) manufactured by Hitachi software engineering company.

EXAMPLE 4

Determination of N-terminal Amino Acid Sequence for Derf II Protein

Amino acid sequence of Derf II protein purified by reverse phase HPLC was determined. The sequence determination was carried out with a gas phase sequencer manufactured by Applied Biosystems company (Model 471A).

Initial amount of 10 μg made it possible to determine the sequence from N-terminal to the 45 amino acid residue. The amino acid sequence obtained was coincident with expected sequence, namely the amino acid sequence estimated from the DNA sequence of cDNA as shown in the above Table I.

EXAMPLE 5

Extraction of fusion proteins and identification of antigenicity

E. coli having pFL1, which were selected from two kinds of E. coli expressing Derf II as fusion proteins and having pFL1 and pFL11 respectively, were cultured in an L broth culture, and the fusion proteins were extracted to confirm their antigenecity. The cells obtained were inoculated in 5 ml of an L broth culture containing 50 μg/ml of ampicillin (L broth-Ap culture) and cultured with shaking at 30° C. overnight. The cultures were inoculated in a 1% L-broth-Ap culture and cultured with shaking at 30° C. When the value of $OD_{660nm}$ became 0.6, the same volume of an L-broth-Ap culture which was previously warmed to 54° C. was added. Further they were cultured with shaking for two hours at 42° C. The cells cultured were recovered and extracted by a method of Marston, Carroll et al. (DNA Cloning, IRL Press. Vol. 3, Chapters 4 and 5 (1985)) to obtain fusion proteins. By the observation of a phase-contrast microscope (×1000), it was confirmed that the fusion proteins were visualised in the cells in the form of inclusion bodies.

The fusion proteins obtained were separated with a SDS-polyacrylamide gel electrophoresis system (manufactured by Daiichi Kagaku company, vertical type, gel concentrations of 4–20%). One part of the cells separated was dyed with Coomassie Brilliant Blue and the other part was transferred on a membrane (manufactured by Imobiron Milipore company) by a Western blot technique (Towbin H. et al., Proc. Natl. Acad. Sci., U.S.A., Vol. 69, 1409–1412 (1972)), and then the expression of Derf II antigen proteins was confirmed with anti Derf II antibodies. Proteins showing positive reaction had a molecular weight of about 130 thousands and they were fused proteins with β-galactosidase.

We claim:

1. A protein allergen of Derf II consisting of the amino acid sequence of residues 14–142 of SEQ ID NO:2 or residues 14–142 of SEQ ID NO:4.

2. A protein allergen of Derf II in accordance with claim 1 consisting of the amino acid sequence of amino acids 14–142 of SEQ ID NO:2.

3. A protein allergen of Derf II in accordance with claim 1 consisting of the amino acid sequence of amino acids 14–142 of SEQ ID NO:4.

4. A therapeutic composition comprising a protein allergen of claim 1 and a pharmaceutically acceptable carrier or diluent.

5. A fusion protein having the immunological properties of the major mite allergen Derf II comprising amino acids 14–142 of SEQ ID NO:2 or amino acids 14–142 of SEQ ID NO:4 fused to additional amino acid residues which do not affect the immunological properties of the portion of the fusion protein containing the Derf II allergen.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
       (A) LENGTH: 517 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 1..426

(xi) SEQUENCE DESCRIPTION: SEQ ID NO:1:

```
GGT ACC ATG GTT TCA TTG TTG GTA GCA GCC GTT GTT GCC GAT CAA GTC        48
Gly Thr Met Val Ser Leu Leu Val Ala Ala Val Val Ala Asp Gln Val
 1               5                  10                  15

GAT GTT AAA GAT TGT GCC AAC AAT GAA ATC AAA AAA GTA ATG GTC GAT        96
Asp Val Lys Asp Cys Ala Asn Asn Glu Ile Lys Lys Val Met Val Asp
                20                  25                  30

GGT TGC CAT GGT TCT GAT CCA TGC ATC ATC CAT CGT GGT AAA CCA TTC       144
Gly Cys His Gly Ser Asp Pro Cys Ile Ile His Arg Gly Lys Pro Phe
            35                  40                  45

ACT TTG GAA GCC TTA TTC GAT GCC AAC CAA AAC ACT AAA ACC GCT AAA       192
Thr Leu Glu Ala Leu Phe Asp Ala Asn Gln Asn Thr Lys Thr Ala Lys
    50                  55                  60

ATT GAA ATC AAA GCC AGC CTC GAT GGT CTT GAA ATT GAT GTT CCC GGT       240
Ile Glu Ile Lys Ala Ser Leu Asp Gly Leu Glu Ile Asp Val Pro Gly
65                  70                  75                  80

ATC GAT ACC AAT GCT TGC CAT TTT GTC AAA TGT CCA TTG GTT AAA GGT       288
Ile Asp Thr Asn Ala Cys His Phe Val Lys Cys Pro Leu Val Lys Gly
                85                  90                  95

CAA CAA TAT GAT ATC AAA TAT ACA TGG AAT GTG CCG AAA ATT GCA CCA       336
Gln Gln Tyr Asp Ile Lys Tyr Thr Trp Asn Val Pro Lys Ile Ala Pro
                100                 105                 110
```

```
AAA TCT GAA AAC GTT GTC GTT ACA GTC AAA CTT ATC GGT GAT AAT GGT         384
Lys Ser Glu Asn Val Val Val Thr Val Lys Leu Ile Gly Asp Asn Gly
        115                 120                 125

GTT TTG GCT TGC GCT ATT GCT ACC CAT GGT AAA ATC CGT GAT                 426
Val Leu Ala Cys Ala Ile Ala Thr His Gly Lys Ile Arg Asp
130                 135                 140

TAAAAAAAAA TAAATAAGAA AATTTTCACC AACATCGAAC AAAATTCAAT AACCAAAATT       486

TGAATCCAAA AAAAAAAAAA AAAAACCATG G                                      517

(2) INFORMATION FOR SEQ ID NO:2:

(i) SEQUENCE CHARACTERISTICS:
        (A) LENGTH: 142 amino acids
        (B) TYPE: amino acid
        (D) TOPOLOGY: linear (ii) MOLECULE TYPE: protein (xi) SEQUENCE DESCRIPTION: SEQ ID NO:2:

Gly Thr Met Val Ser Leu Leu Val Ala Ala Val Val Ala Asp Gln Val
1               5                   10                  15

Asp Val Lys Asp Cys Ala Asn Asn Glu Ile Lys Lys Val Met Val Asp
            20                  25                  30

Gly Cys His Gly Ser Asp Pro Cys Ile Ile His Arg Gly Lys Pro Phe
        35                  40                  45

Thr Leu Glu Ala Leu Phe Asp Ala Asn Gln Asn Thr Lys Thr Ala Lys
    50                  55                  60

Ile Glu Ile Lys Ala Ser Leu Asp Gly Leu Glu Ile Asp Val Pro Gly
65                  70                  75                  80

Ile Asp Thr Asn Ala Cys His Phe Val Lys Cys Pro Leu Val Lys Gly
                85                  90                  95

Gln Gln Tyr Asp Ile Lys Tyr Thr Trp Asn Val Pro Lys Ile Ala Pro
            100                 105                 110

Lys Ser Glu Asn Val Val Val Thr Val Lys Leu Ile Gly Asp Asn Gly
        115                 120                 125

Val Leu Ala Cys Ala Ile Ala Thr His Gly Lys Ile Arg Asp
130                 135                 140

(2) INFORMATION FOR SEQ ID NO:3:

(i) SEQUENCE CHARACTERISTICS:
        (A) LENGTH: 513 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..426

(xi) SEQUENCE DESCRIPTION: SEQ ID NO:3:

GGT ACC ATG GTT TCA TTG TTG GTA GCA GCC GTT GTT GCC GAT CAA GTC          48
Gly Thr Met Val Ser Leu Leu Val Ala Ala Val Val Ala Asp Gln Val
        145                 150                 155

GAT GTT AAA GAT TGT GCC AAC AAT GAA ATC AAA AAA GTA ATG GTC GAT          96
Asp Val Lys Asp Cys Ala Asn Asn Glu Ile Lys Lys Val Met Val Asp
160                 165                 170

GGT TGC CAT GGT TCT GAT CCA TGC ATC ATC CAT CGT GGT AAA CCA TTC         144
Gly Cys His Gly Ser Asp Pro Cys Ile Ile His Arg Gly Lys Pro Phe
175                 180                 185                 190
```

```
ACT TTG GAA GCC TTA TTC GAT GCC AAC CAA AAC ACT AAA ACC GCT AAA        192
Thr Leu Glu Ala Leu Phe Asp Ala Asn Gln Asn Thr Lys Thr Ala Lys
            195                 200                 205

ATT GAA ATC AAA GCC AGC CTC GAT GGT CTT GAA ATT GAT GTT CCC GGT        240
Ile Glu Ile Lys Ala Ser Leu Asp Gly Leu Glu Ile Asp Val Pro Gly
            210                 215                 220

ATC GAT ACC AAT GCT TGC CAT TTT ATG AAA TGT CCA TTG GTT AAA GGT        288
Ile Asp Thr Asn Ala Cys His Phe Met Lys Cys Pro Leu Val Lys Gly
            225                 230                 235

CAA CAA TAT GAT GCC AAA TAT ACA TGG AAT GTG CCG AAA ATT GCA CCA        336
Gln Gln Tyr Asp Ala Lys Tyr Thr Trp Asn Val Pro Lys Ile Ala Pro
            240                 245                 250

AAA TCT GAA AAC GTT GTC GTT ACA GTC AAA CTT GTT GGT GAT AAT GGT        384
Lys Ser Glu Asn Val Val Val Thr Val Lys Leu Val Gly Asp Asn Gly
255                 260                 265                 270

GTT TTG GCT TGC GCT ATT GCT ACC CAC GCT AAA ATC CGT GAT                426
Val Leu Ala Cys Ala Ile Ala Thr His Ala Lys Ile Arg Asp
            275                 280

TAAAAAAAAA AAATAAATAT GAAATTTTC ACCAACATCG AACAAATTC AATAACCAAA        486

ATTTGAATCA AAAAAAAAAA ACCATGC                                          513

(2) INFORMATION FOR SEQ ID NO:4:

(i) SEQUENCE CHARACTERISTICS:
        (A) LENGTH: 142 amino acids
        (B) TYPE: amino acid
        (D) TOPOLOGY: linear (ii) MOLECULE TYPE: protein (xi) SEQUENCE DESCRIPTION: SEQ ID NO:4:

Gly Thr Met Val Ser Leu Leu Val Ala Ala Val Val Ala Asp Gln Val
1               5                   10                  15

Asp Val Lys Asp Cys Ala Asn Asn Glu Ile Lys Lys Val Met Val Asp
            20                  25                  30

Gly Cys His Gly Ser Asp Pro Cys Ile Ile His Arg Gly Lys Pro Phe
            35                  40                  45

Thr Leu Glu Ala Leu Phe Asp Ala Asn Gln Asn Thr Lys Thr Ala Lys
    50                  55                  60

Ile Glu Ile Lys Ala Ser Leu Asp Gly Leu Glu Ile Asp Val Pro Gly
65                  70                  75                  80

Ile Asp Thr Asn Ala Cys His Phe Met Lys Cys Pro Leu Val Lys Gly
            85                  90                  95

Gln Gln Tyr Asp Ala Lys Tyr Thr Trp Asn Val Pro Lys Ile Ala Pro
            100                 105                 110

Lys Ser Glu Asn Val Val Val Thr Val Lys Leu Val Gly Asp Asn Gly
            115                 120                 125

Val Leu Ala Cys Ala Ile Ala Thr His Ala Lys Ile Arg Asp
130                 135                 140
```